(12) United States Patent
Lauterjung

(10) Patent No.: US 6,740,111 B1
(45) Date of Patent: May 25, 2004

(54) DEVICE FOR RETAINING A PROSTHESIS WITHIN A BODY PASSAGE

(75) Inventor: Karl-Lutz Lauterjung, Munich (DE)

(73) Assignee: Vascutek Limited, Renfrewshire (GB)

( * ) Notice: Subject to any disclaimer, the term of this patent is extended or adjusted under 35 U.S.C. 154(b) by 588 days.

(21) Appl. No.: 09/365,860

(22) Filed: Aug. 3, 1999

Related U.S. Application Data

(63) Continuation of application No. 08/878,908, filed on Jun. 19, 1997.

Foreign Application Priority Data

Jun. 20, 1996 (DE) .......................................... 196 24 642
Aug. 20, 1996 (DE) .......................................... 196 33 588

(51) Int. Cl.$^7$ ................................................. A61F 2/06
(52) U.S. Cl. ...................... 623/1.1; 623/2.38; 623/1.12; 623/1.22; 138/126
(58) Field of Search ................................ 623/1.2, 1.16, 623/1.13, 2.38, 2.4, 1.1, 1.14, 1.17, 1.22; 606/191, 198, 197; 214/166–169, 176, 178, 360, 364.1; 267/86; 310/272, 1; 138/127–129, 132, 154, 174

(56) References Cited

U.S. PATENT DOCUMENTS

| | | | | |
|---|---|---|---|---|
| 3,153,737 A | * | 10/1964 | Bey .................. | 310/154.37 |
| 3,740,809 A | * | 6/1973 | Wolstencroft .............. | 29/148.4 |
| 4,041,931 A | * | 8/1977 | Elliott et al. ................ | 128/899 |
| 4,567,917 A | * | 2/1986 | Millard ....................... | 138/126 |
| 5,099,902 A | * | 3/1992 | Shurman .................... | 152/540 |
| 5,151,105 A | * | 9/1992 | Kwan-Gett .................... | 623/1 |
| 5,676,671 A | * | 10/1997 | Inoue ......................... | 606/108 |
| 5,976,179 A | * | 11/1999 | Inoue .......................... | 623/1 |

* cited by examiner

Primary Examiner—Paul B. Prebilic
(74) Attorney, Agent, or Firm—Trop, Pruner & Hu, P.C.

(57) ABSTRACT

A prosthesis that resiliently engages a body passage includes an annular clamping ring which may be folded along a diametric axis for insertion into the body passage. The clamping ring is adapted to resiliently spring outwardly, once in position inside the body passage, and to be continually resiliently biased against the interior surface of the body passage. One or more of the clamping rings may be attached to opposed ends of a tubular graft. The rings and connected graft may be positioned in the body passage using a applicator which selectively permits expansion and/or in some embodiments contraction of the annular ring in position within a body passage. Alternatively a retaining member may be used to retain the annular ring in a compressed condition until it is in a desired position within a body passage. Among other potential uses, the present invention may be useful as a vascular stent for treating abdominal aortic aneurysms.

5 Claims, 10 Drawing Sheets

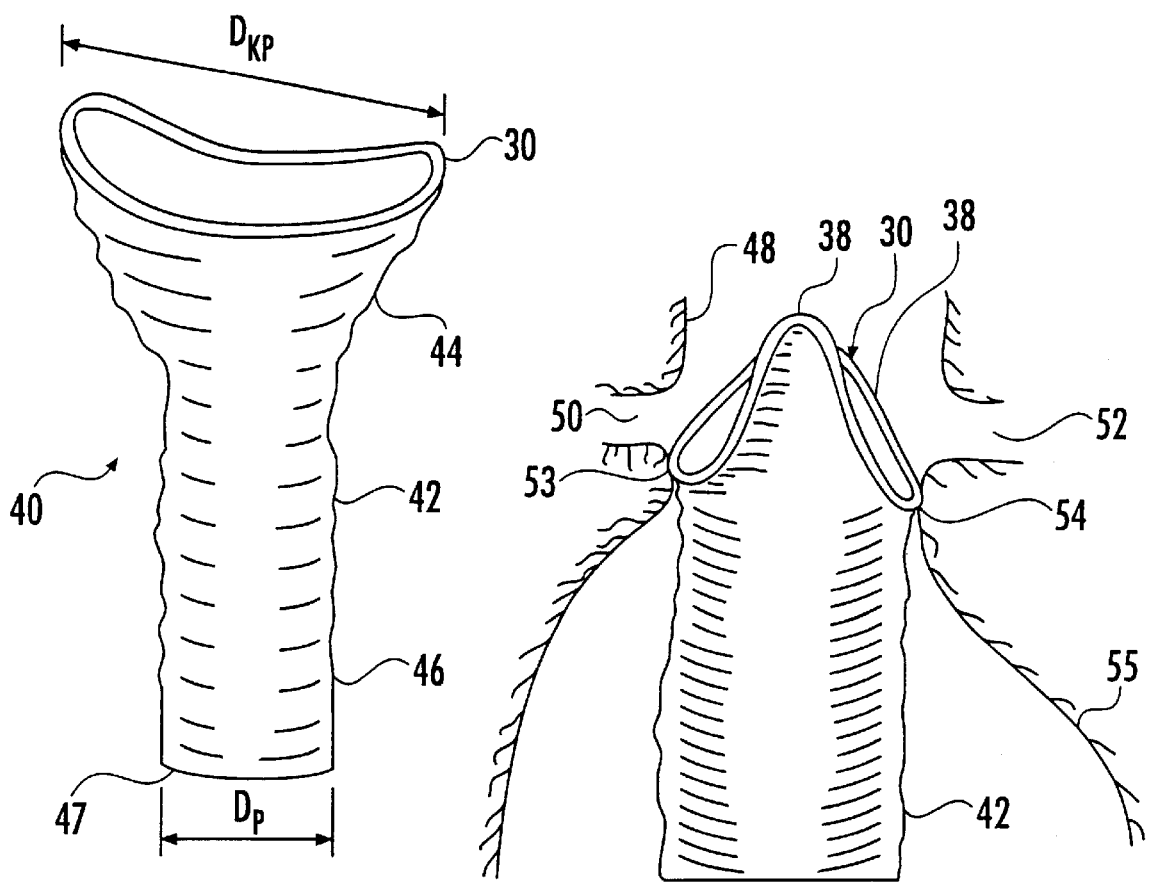
FIG. 3
FIG. 4
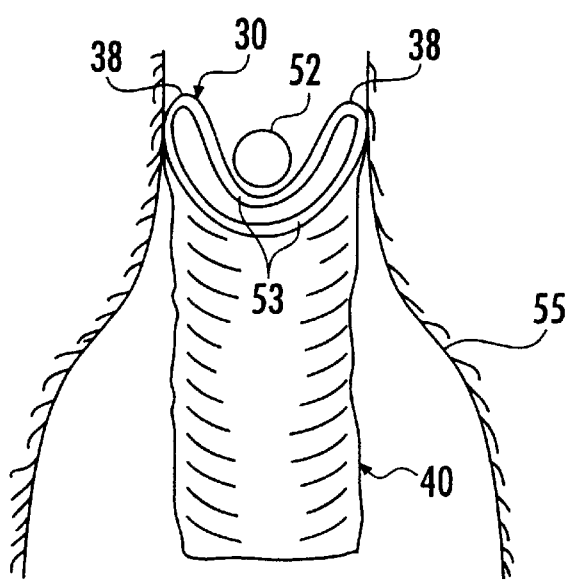
FIG. 5

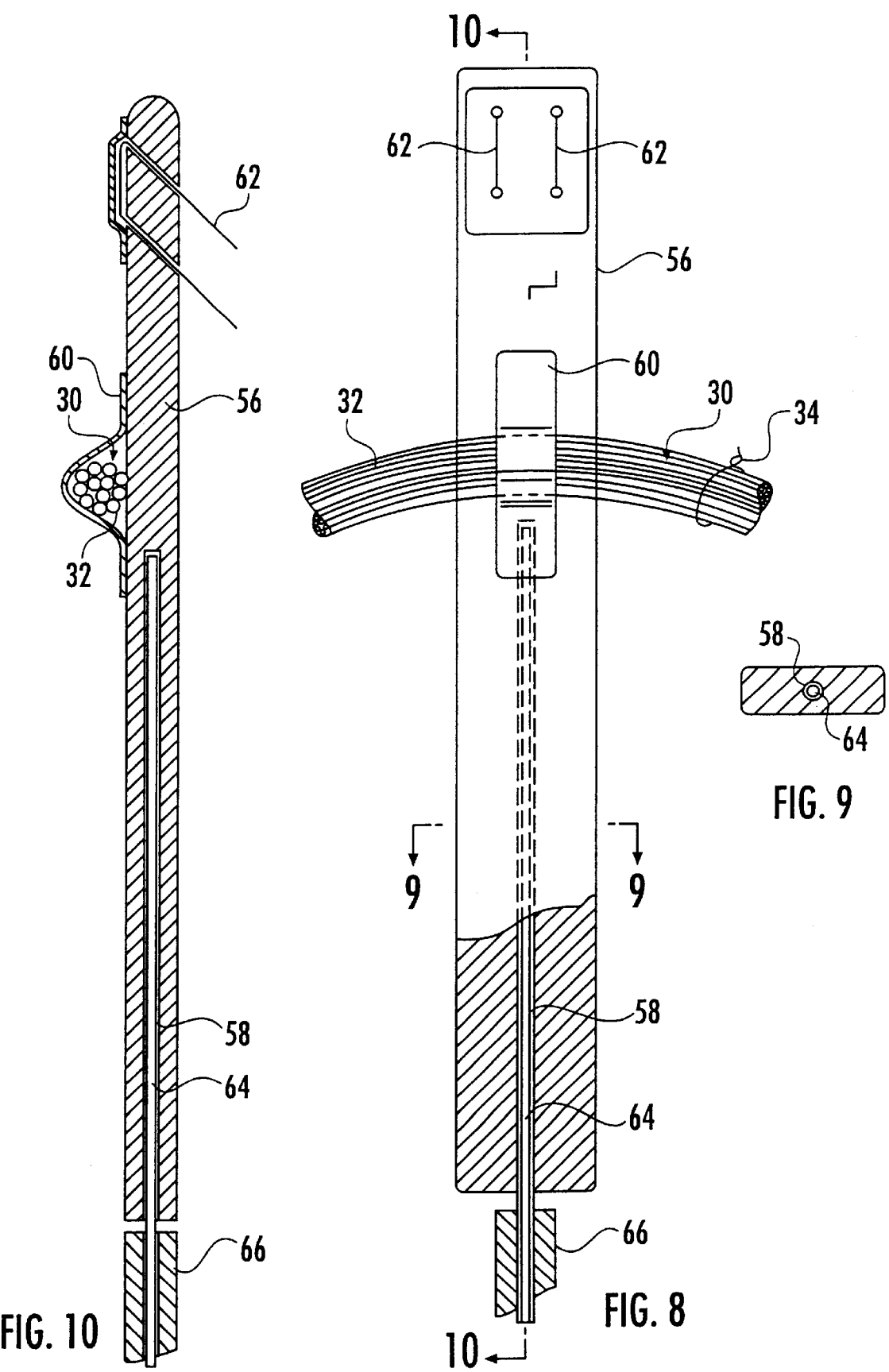

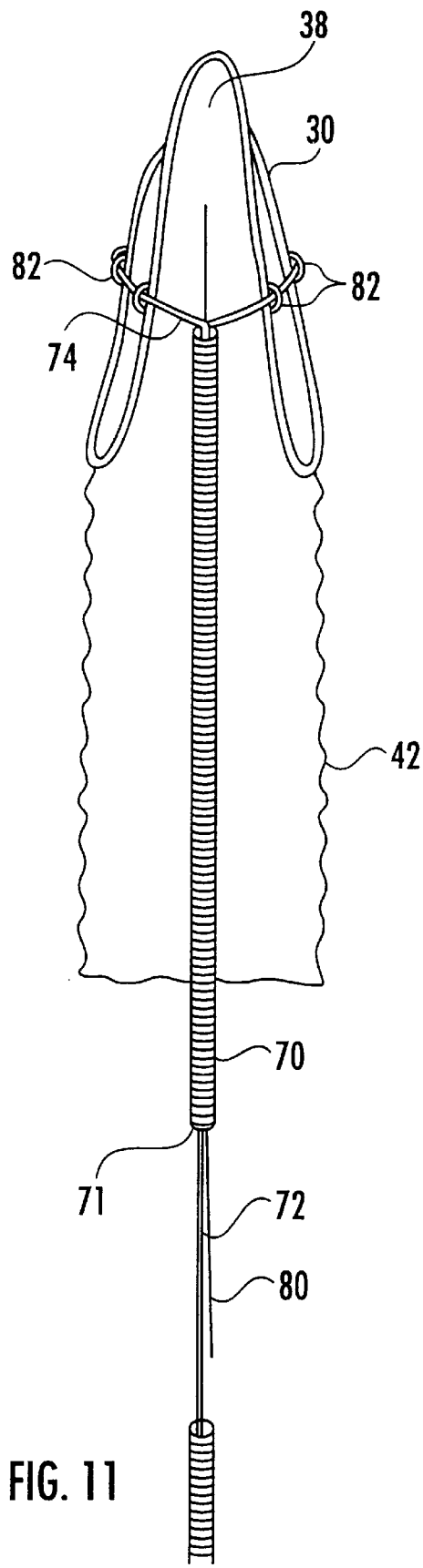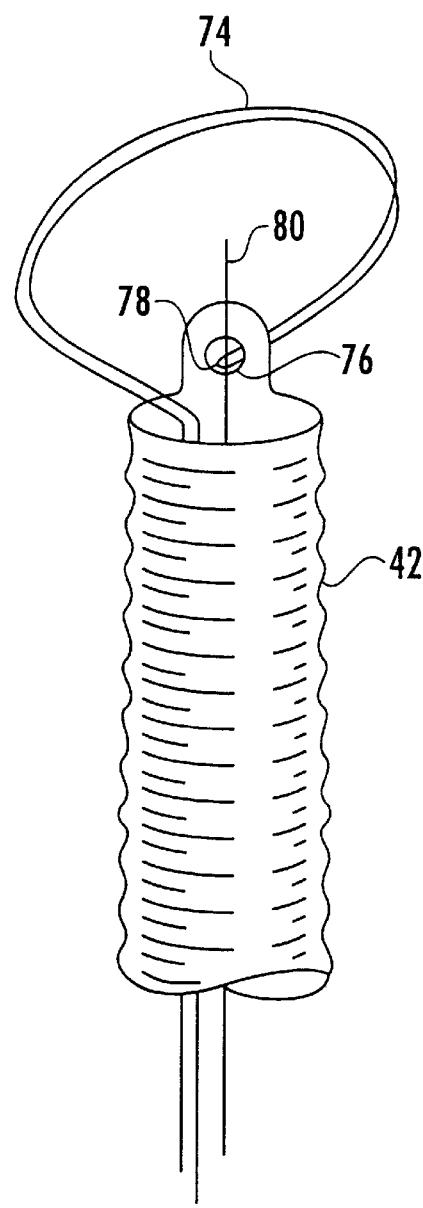
FIG. 11
FIG. 12

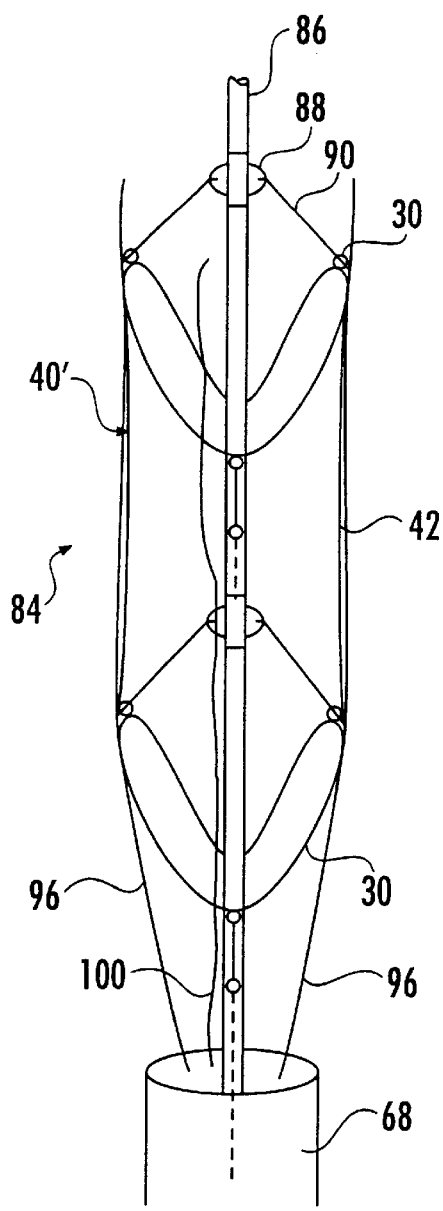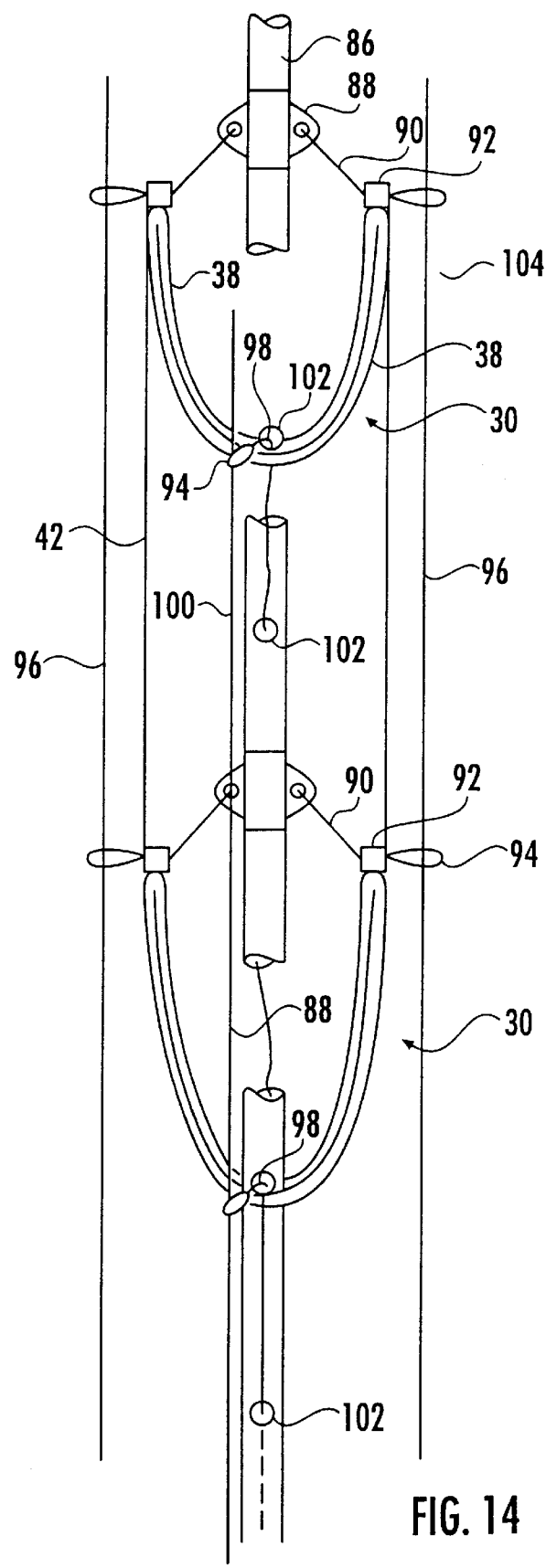
FIG. 13
FIG. 14

DEVICE FOR RETAINING A PROSTHESIS WITHIN A BODY PASSAGE

This is a continuation of prior Application Ser. No. 08/878,908 filed Jun. 19, 1997.

BACKGROUND OF THE INVENTION

The present invention relates to devices that are retained inside a body passage and in one particular application to vascular stents for the repair of arterial dilations known as aneurysms.

As a result of arteriosclerosis, portions of blood vessels may become weakened and extremely dilated. These dilated vessels may be treated by bridging the dilation or weakened extended area using a vascular tubular prosthesis. In this way the diseased portion of the vessel is effectively isolated from the pressure inside blood vessels.

Vascular tubular prostheses may be inserted into the diseased portion of the vessel by surgically opening the vessel and suturing the prosthesis into position. However, it may be preferred to insert the prosthesis from a remote opening, such as the femoral artery, adjacent the groin, using a catheter system. This is because the elimination of the need to open a major body cavity may diminish the potential surgical complications.

Generally it is desirable to insert the prosthesis, using a catheter, in a collapsed or compressed condition and then to expand the prosthesis when in position. One reason for this is that it is desirable to avoid substantially occluding the blood flow during the insertion process. Therefore, by collapsing the prosthesis, the prosthesis may be readily positioned inside the vessel, in some cases without substantially occluding the blood flow.

There are generally two techniques for expanding the prosthesis once in position at the location to be repaired. One technique uses a malleable metal prosthesis which has two configurations. One configuration has a relatively smaller diameter and the other has a relatively radially expanded configuration contacting and securing to a neck portion on either side of the diseased vessel region. The prosthesis may be a malleable metal ring which may be expanded by a balloon catheter to set the prosthesis in its expanded diameter, inside the neck portion, proximate to the diseased portion of the vessel.

Another general approach is to use a self-expandable prosthesis which may be compressed against a resilient bias. Once in position, the prosthesis is allowed to resiliently expand into contact with the vessel wall.

While a wide variety of solutions have been proposed to the problem of effectively bypassing diseased tissue, various existing prosthetic device designs may have certain deficiencies. For example, in some cases, the neck portion on either side of the diseased vessel portion may be relatively short. This makes it difficult for prosthetic devices to adequately engage the narrow neck on either side of the aneurysm.

In addition, some of the existing prostheses may cause blockage of the blood flow during insertion of the prosthesis, which can have physiologically adverse affects. Still another issue is that many existing prostheses do not adequately seal against the internal surface of a vessel, allowing leakage of blood past the prosthesis into the region between the prosthesis and the weakened blood vessel. The consequences of this type of leakage can be traumatic. In some designs, the device may not be adaptable to non-circular or irregularly shaped neck regions.

Still another issue with some known prostheses is that they may require the hospital to stock a variety of prosthesis sizes for different situations and different patient physiologies. Also some designs may require that the prosthesis be custom fitted for each particular patient.

Another difficulty may arise with regard to accurately positioning the prosthesis once it has been expanded. In some cases inaccurate positioning may be problematic. Similarly, in many existing prostheses it is possible that the prosthesis may be dislodged from its desired position so that it does not effectively accomplish its function of protecting the weakened vessel.

Thus, for these and other reasons, there is a continuing need for enhanced solutions to the problem of repairing diseased vessels and in general to the problem of effectively securing prosthetic devices to the internal walls of body passages.

SUMMARY OF THE INVENTION

According to one aspect of the present invention, a device for retaining a prosthesis in a body passage includes an annular, resilient element. The element has an undeformed diameter greater than the diameter of the body passage.

According to another aspect of the present invention, a prosthesis for insertion into a body passage includes an annular, resilient spring element and a tubular graft. The graft may be attached to the element. The element has an undeformed diameter greater than the diameter of the graft.

According to still another aspect of the present invention, a vascular prosthesis for repairing a diseased first vessel includes a resilient, annular ring having a first pair of loops extending in one direction, and a second pair of loops, extending in the opposite direction. The first and second pairs of loops are connected together. A tubular graft is connected to the ring. The graft is arranged to extend along the length of the first vessel and the first pair of loops are arranged to extend at least partially past the point where a second vessel intersects the first vessel. One of the second pair of loops defines an opening to permit communication between the first and second vessels, at least partially past the prosthesis.

According to yet another aspect of the present invention, a method of securing a prosthetic device in a body passage includes the step of folding a resilient annular ring to assume a first configuration having a cross-sectional area smaller than the cross-sectional area of the undeformed ring. The ring is positioned at a desired location within a body passage and allowed to resiliently deform to a second configuration, having a larger diameter then the first configuration, but still having a cross-sectional area smaller then that of the undeformed ring.

According to but another aspect of the present invention, a method for repairing a diseased vessel includes the step of folding an annular ring on its diametric axis to assume a smaller cross-sectional configuration and forming a pair of loops extending away from the axis. The ring is arranged in the vessel with its diametric axis proximate to an intersecting vessel such that the loops extend at least partially past the intersecting vessel without occluding the intersecting vessel.

According to yet another aspect of the present invention, a method for securing a prosthetic device inside a body passage includes the step of deforming an annular resilient spring by folding said spring along its diametric axis. The spring is positioned inside a body passage. The spring expands resiliently against the body passage. The spring continuously presses outwardly against the body passage.

According to but another aspect of the present invention, a prosthetic device includes a prosthetic heart valve, a flexible tubular sleeve having a first end connectable to the valve and a second end. A deformable, resilient annular ring is connected to the second end and arranged to connect the graft to the interior surface of a portion of the ascending aorta.

According to yet another aspect of the present invention, a prosthesis for insertion into a body passage includes at least two annular resilient spring elements and a flexible, tubular graft attached to each of the elements. A rigid member longitudinally connects the elements. The rigid member is less flexible than the graft.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

FIG. 3 is a front elevational view of a clamping ring before insertion into a body passage;

FIG. 4 is a front elevational view of a clamping ring after introduction into a body passage;

FIG. 5 is a side elevational view of the embodiment shown in FIG. 4;

FIG. 8 is an enlarged, partially sectioned view of the retention device shown in FIG. 6;

FIG. 9 is a cross-sectional view taken generally along line 9—9 in FIG. 8;

FIG. 10 is a cross-sectional view taken generally along line 10—10 in FIG. 8;

FIG. 11 is an enlarged front elevational view of a prosthesis retained by a retention loop;

FIG. 12 is an enlarged, front elevational view of a portion of the retention loop;

FIG. 13 is a front elevational view of another embodiment of the prosthesis and insertion device;

FIG. 14 is an enlarged view of the prosthesis shown in FIG. 13;

DESCRIPTION OF A PREFERRED EMBODIMENT

Figure 1:
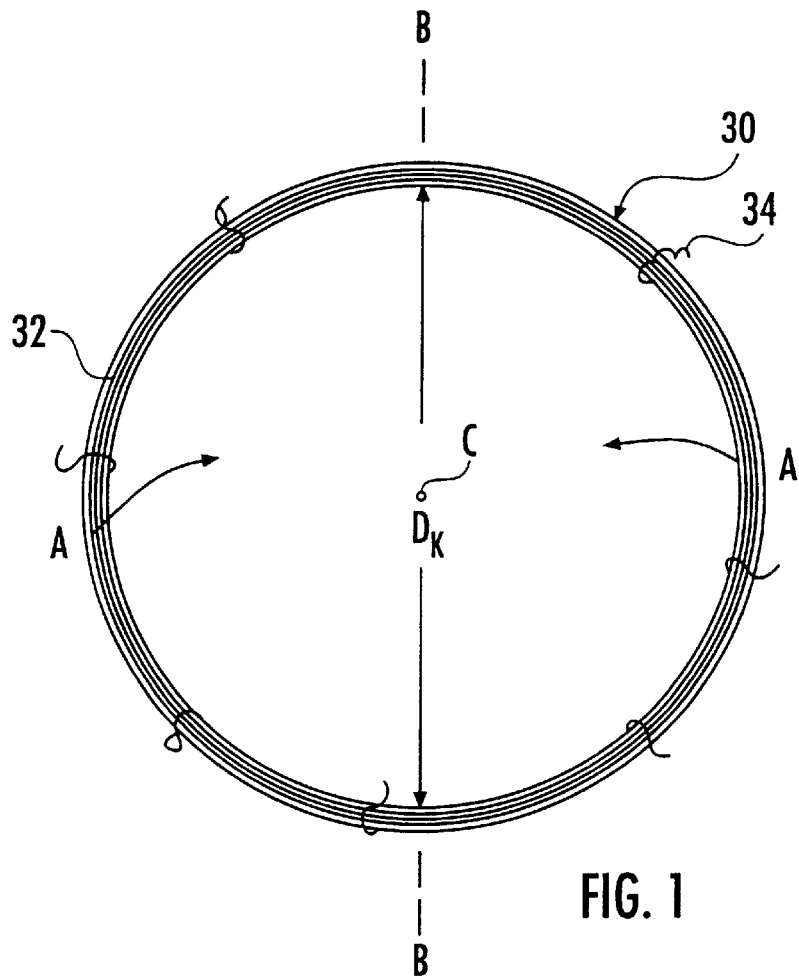
FIG. 1 is generalized top plan view of a clamping ring in accordance with one embodiment of the present invention.

Referring to the drawing wherein like reference characters are used for like parts throughout the several views, an annular, resilient clamping ring 30 may be formed of a plurality of strands 32 of resilient wire as shown in FIGS. 1, 8 and 10. One embodiment of the ring 30 may be formed by a wrapping a single length of wire around the mandrel (not shown) having a central axis "C" and then securing the strands into a bundle using ties 34. The ties 34 may be formed from surgical suture material. Of course, the ring 30 may be formed by a variety of other techniques include the use of a single strand of wire, the use of multiple strands of helically intertwined wire, as in multi-strand wire rope, or any other suitable technique which forms a highly resilient annular ring.

The number of coils or strands 32 can be varied according to the wire utilized and the particular application involved. However, in one embodiment, the number of strands 32 utilized is approximately 8 to 10 as shown in FIG. 10. However, the number of coils or strands 32 may vary from as few as 2 to as many as 100 or possibly more.

While a variety of different wire diameters may be utilized, the individual strands 32 may have a diameter of from about 0.05 to 1 mm. In one advantageous embodiment a wire strand 32 diameter of about 0.1 mm may be used.

The strands 32 may be made of any highly resilient metal or plastic material, including a nickel titanium alloy such as Nitinol. Generally the resilient or superelastic or martensitic form of Nitinol is utilized.

The diameter $D_K$ of the ring 30 is subject to considerable variation depending on the particular body passage involved. In connection with an aortic vascular graft, a ring diameter of about 30 mm may be adequate and in other situations ring diameters ($D_K$) of from about 6 to 50 mm may be suitable.

Referring to FIG. 1, the ring 32, before compression, may have a diameter, $D_K$, which is considerably greater then the diameter, $D_R$, of the body passage 36 to be treated. As indicated in FIG. 1, two diametrically opposed points "A" on the undeformed ring 30 may be deflected towards one another. As indicated by the arrows, this causes the ring 30 to fold along its diametric axis "B". In this configuration, the ring 30 may be inserted into the body passage 36 in a reduced cross-sectional configuration.

As a result of the folding along the diametric axis "B," the loops 38, which include the folded tips "A," extend proximally relative to the points "B" which are along the diametric axis of folding. As used herein, the term "proximal" refers to the direction upstream with respect to blood flow and the term "distal" refers to the direction downstream with respect to blood flow.

Once in position inside the body passage 36, the ring 30 makes continuous contact with the internal vessel 36 wall even though the ring 30 may take a generally sinusoidal shape. To a first approximation, the height H, indicated in FIG. 2, is a quadratic function of the radial compression.

Figure 2:
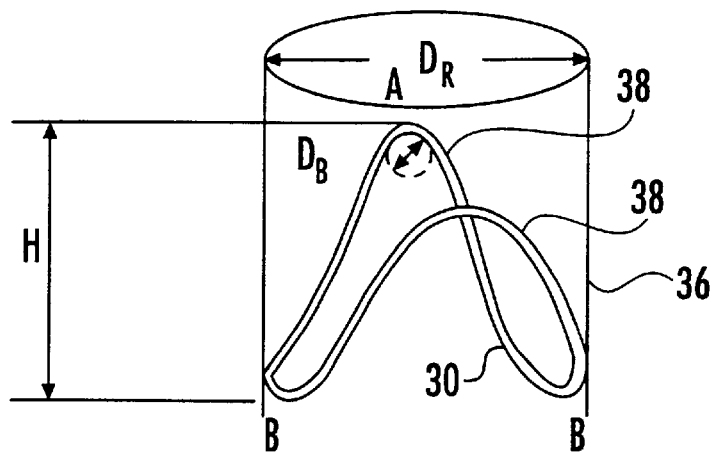
FIG. 2 is a reduced, perspective view of the embodiment of FIG. 1 in place within an idealized body passage.

The smallest permissible bending diameter without plastic deformation, $D_B$, shown in FIG. 2, depends on the material, the thickness of the clamping ring 30 and the individual strands 32 which may make up the ring 30. According to Hooke's law, the strands 32 can be regarded as parallelly connected springs whose deflection characteristic values are additive and whose individual low radial tension forces add up to a total tension force which depends on the number of strands 32. When the entire ring 30 is compressed, each individual strand 32 has a bending diameter approximately corresponding to the minimum bending diameter $D_B$ of the individual strand 32.

As an approximation, the minimum bending diameter $D_B$ is approximately ten times the wire diameter. This suggests that the ring 30 wire diameter be kept low. However, the ring's clamping force on the body passage 36 is a function of its diameter, suggesting conversely that the wire diameter be increased. This tradeoff can be optimized by using a plurality of strands 32, whose diameter controls the minimum bending diameter, to form a bundle whose composite diameter controls the clamping force. Thus a clamping ring 30 with a high tension force can be shaped to a relatively small compressed configuration. After being released from a catheter, for example having a conventional diameter of from 4 to 6 mm, the ring 30 may return to its original shape and by means of sufficient tension force, securely presses the ring 30 along the wall of a body passage 36.

A prosthesis 40 may include an annular ring 30 and a graft 42, as shown in FIG. 3. The graft 42 may be generally tubular and made of a fabric or film secured on one end to the ring 30. The graft 42 may have a diameter $D_P$ which is smaller then the diameter $D_K$ of the clamping ring 30. Due to the connection between the clamping ring 30 and the end of the graft 42, there is a diameter $D_{KP}$ at the junction point between the clamping ring and the graft 42. The clamping ring 30 may expand the end of the tubular graft 42 to a stop or deformation limit, after which no further expansion occurs. Thus, the ring 30 may expand upon the graft 42 in the region proximate to the ring 30 so that the diameter of the graft 42 gradually tapers in the region 44 down to a relatively constant diameter region 46, terminating in a free end 47. Alternatively, the graft 42 could be preformed in the flared shaped shown in FIG. 3.

Any one of a variety of fabric materials compatible with human implantation may be utilized to form the graft 42. For example, the graft 42 may be formed of flexible woven or knitted textiles made of Dacron, Teflon, or other materials. It is advantageous if the tubular graft 42 is made of a material which does not change its circumference readily. It is also advantageous if the portion 46 of the graft 42 has a diameter $D_P$ which is approximately the same as the diameter $D_R$ of the body passage 36 to be repaired.

The ring 30 can be connected with the region 44 by means of sutures or bonding. It is advantageous if the clamping ring 30 is arranged on the interior surface of the graft 42 so that when the ring 30 extends against the body passage 36 wall, the graft 42 intervenes between the passage 36 and the ring 30. Thus, it may be advantageous that the diameter $D_K$ of the ring 30 be considerably greater than the diameter of the portion 46 of the graft 42.

Referring to FIG. 4, the prosthesis 40 may be positioned within the abdominal aorta 48 proximate to the left renal artery 50 and the right renal artery 52. The loops 38 extend past the arteries 50 and 52 while the portion 53 is located just distally of the openings to the arteries 48 and 50. Thus, as shown in FIG. 5, the openings to the arteries 48 and 50 are not in any way occluded by the positioning of the annular ring 30 proximate thereto because of the generally C-shaped configuration in cross-section of the ring 30.

Because of this configuration, the ring 30 may be secured to a substantially undeformed neck region 54 of relatively short height bounding an aneurysm 55. This is because at least part of the ring 30 extends proximally beyond the neck 54 without in any way affecting the flow through the arteries 48 and 50. Moreover, because the clamping ring 30 never completely expands to its unfolded configuration (shown in FIG. 1), it is adaptable to irregularly configured neck 54 cross-sections.

For example, if the neck 54 is non-circular in cross-section, the sinusoidally shaped ring 30, in compression, can adapt to the irregular body passage shape. By making the ring 30 with an uncompressed diameter ($D_K$) greater than the diameter of the body passage ($D_R$) which it is designed to engage, a continuing resilient engagement occurs between the ring 30 and the body passage 36 which may continue even if the body passage becomes distended over time. This may occur regularly due to normally pulsing blood pressure or due to vasodilation over time.

Further by making the diameter of the ring 30 ($D_{KP}$) greater than the diameter of the graft 42 ($D_P$), the graft diameter in use will correspond closely to the compressed cross-sectional diameter ($D_K$) of the ring 30, in position within the body passage 36. This lessens any unnecessary bunching of the graft 42 around the neck 54.

Figures 6, 7:
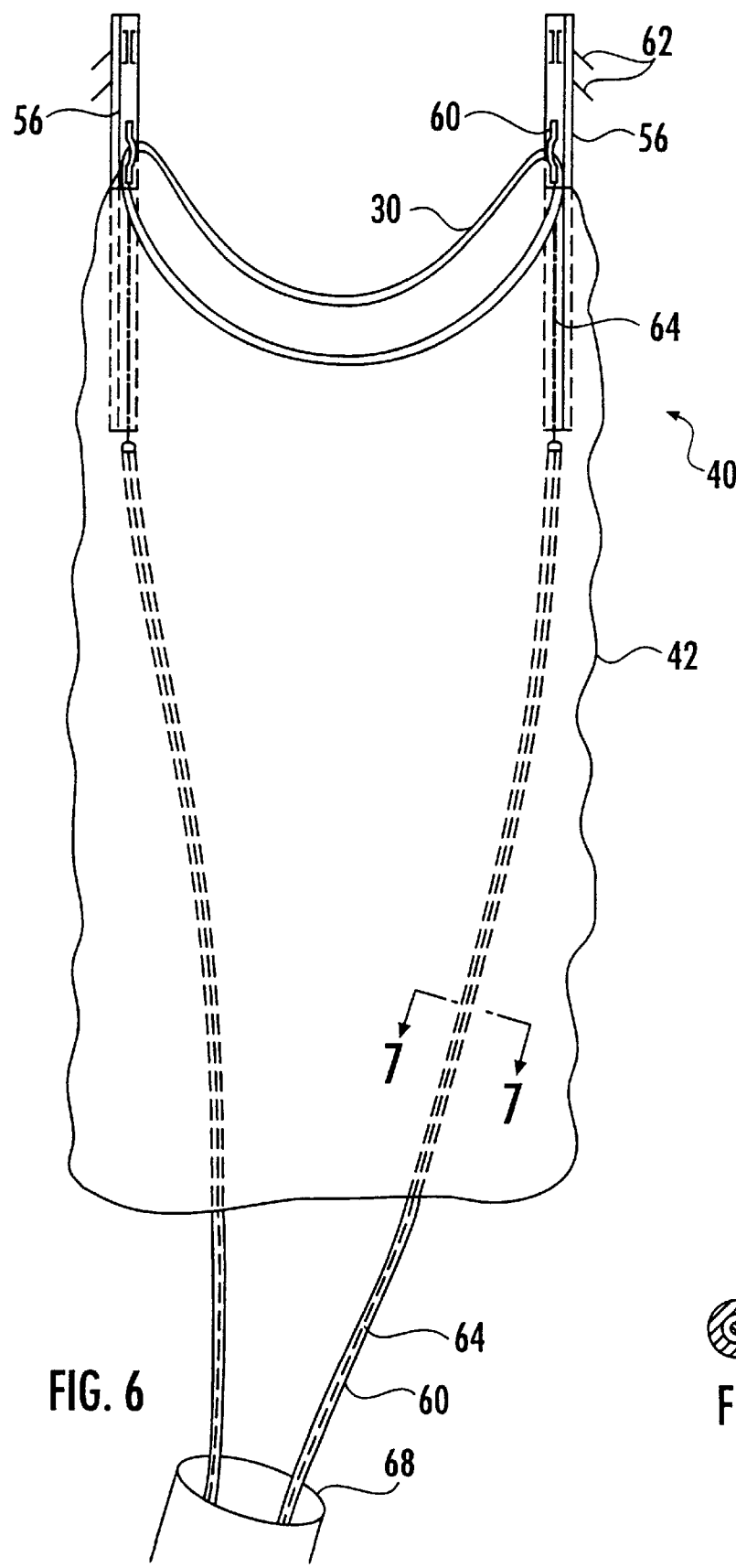
FIG. 6 is a front elevational view of a prosthesis with an application apparatus.
FIG. 7 is a cross-sectional view taken generally along the line 7—7 in FIG. 6.

Turning now to a method for positioning the prosthesis 40 in a desired location within a passage, a retention device 56, shown in FIG. 6, may be secured to the ring 30 on at least two diametrically opposed orientations so that the device 56 extends generally parallel to the axis of the prosthesis 40. The devices 56 may include a passage 58 in one end and a bracket 60 which secures the device 56 to the ring 30. Alternatively the passage 58 may be replaced by wire restraining brackets (not shown). In some cases barbs 62 may be included on one end of the device 56. However, in many cases, the barbs 62 may be unnecessary.

The device 56 may be engaged by a wire 64 which extends into the passage 58 and by a tube 66 which encircles the wire 64, as indicated in FIG. 7. Advantageously, the device 56 and the tube 66 are made of sufficiently rigid material that pushing against the device 56 by the wire 64 or the tube 66 results in displacement of the prosthesis 40 within the passage 36. The wire 64 may have a diameter of about 0.3 to 1 mm.

The prosthesis 40 may be compressed to fit into the tubular catheter 68, for transferring the prosthesis from a remote entry point to the repair site. The catheter 68 may be inserted into an incision in the femoral artery, for example, and passed to a position within the abdominal aorta, for example, where one may wish to position the annular ring 30. Once in position, the prosthesis 40 may be pushed out of the catheter 68 using the tubes 66. Particularly, the tubes 66 are extended inwardly from the exterior of the body by the surgeon while maintaining the catheter 68 in a fixed position so that the prosthesis 40 is left in position as the catheter 68 is backed away. If desired, the brackets 60 may be made of X-ray opaque material such as platinum, iridium or gold to serve as an X-ray marker.

While the above described procedure for placing the prosthesis 40 may be useful in some applications, it would be desirable to further facilitate accurate and controllable placement of the prosthesis 40 in a particular location. Once the ring 30 is allowed to expand against the passage wall, re-positioning must be done against the resistant force of the ring 30. Thus, it is advantageous to continue to confine the ring 30 after the prosthesis 40 leaves the catheter 68, until the prosthesis 40 is accurately positioned. To this end, a Bowden tube 70 telescopically retains a wire loop 72, as shown in FIGS. 11 and 12. The loop 72 extends axially through the tube 70, forms an annular ring 74 and passes through a hole 76 in the proximal free end of the Bowden tube 72. At this point, the looped end 78 of the wire loop 72 receives a blocking wire 80, where the loop 78 extends out of the hole 76.

Referring to FIG. 11, the Bowden tube 70 extends along the exterior of the prosthesis 40 to a point proximate to the loops 38. The annular ring 74 extends around the periphery of the loops 38 at a relatively central location along their length and is engaged in eyelets 82 secured to the ring 30. In this way, the blocking wire 80 may be withdrawn axially, releasing the looped end 78 so that the wire loop 72 may be withdrawn, releasing the ring 30 and allowing it to spring open at a desired location. The blocking wire 80 may return, inside the Bowden tube 70, to the entry point or it may exit the Bowden tube 70 through a gap 71, as shown in FIG. 11.

Figure 15:
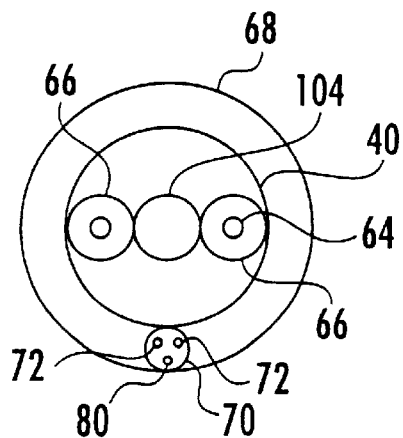
FIG. 15 is an enlarged cross-sectional view of the embodiment shown in FIG. 11 prior to insertion into a body passage.

Referring to FIG. 15, the catheter 68 encircles the prosthesis 40 which in turn encircles a pair of tubes 66 with wires 64 extending through them. If necessary, a guide wire 104 may be included which may be used initially to guide the catheter to the desired location and to maintain a path for returning to the same location with additional elements, if necessary. The Bowden tube 70 with the looped wires 72 and blocking wire 80 also extends inside the catheter 68 between the catheter and the prosthesis 40.

In still another embodiment, a retaining mechanism 84, shown in FIGS. 13 and 14, retains the prosthesis 40 in a compressed configuration to accurately locate it at the desired position within a passage. The mechanism 84 may control a prosthesis 40' having a pair of rings 30, connected by a graft 42, in a compressed position inside a catheter 68. A guide wire catheter 86 extends axially through the prosthesis 40'. A plurality of ringlets 88 extend off of the catheter 86. Each of the ringlets 88 connects to wire loops 90 which in turn connect to eyelets 92 at the free ends of the loops 38.

Referring to FIG. 14, each of the wire loops 90 slidably and releasably extends through the eyelet 92 and forms a loop end 94. A blocking wire 96 extends through the loop ends 94. A portion of each ring 30 along its folding axis "B" is wrapped by a wire loop 98 which is engaged on its free end by blocking wire 100. The wire loop 98 may wrap around and over the ring 30, over the outside of the guide wire catheter 86 and into the interior of the catheter 86 through an opening 102. Each of the rings 30 on opposed ends of the graft 42 includes the same parts and may be operated in the same way.

Thus, to adjust the extent of folding or the proximal-distal height of the rings 30 in the orientation shown in FIG. 14, it is simply necessary to pull outwardly on the wires 98 which may be connected together to a single wire 103 that extends to the exterior of the patient. To decrease the height and to decrease the compression of the ring 30, the tension on the wire loop 98 may be relaxed, allowing the natural spring forces of the rings 30 to cause the bending of the ring 30 to be relieved and the ring, height to be reduced.

After the catheter 68 is positioned in the desired location, the assembly may be ejected from the catheter using the techniques described previously. The amount of compression of the ring 30 may be adjusted so that the apparatus 84 can be temporarily positioned at a desired location. If it is determined that the location is not precisely correct, the apparatus can be re-compressed, by operating the loops 98, to allow repositioning of the apparatus 84 to a new location. In this way, it is possible to selectively adjust the position of the prosthesis 40', even after the prosthesis has previously been released to engage the body passage. If an error is initially made, it is easy to reposition the prosthesis, as necessary. Once the prosthesis is located at the desired location, the blocking wires 100 and 96 can simply be pulled out of the assembly through the catheter 68. This allows the prosthesis 40' to expand, irreversibly. The catheter 86 may be removed thereafter.

If desired, each of the loops 98 can be connected by an independent wire to the exterior of the patient. Or as described previously, the wires 98 may be connected so that only one single wire extends outwardly.

Figure 16:
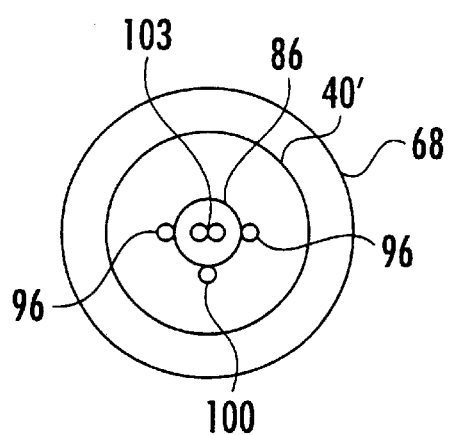
FIG. 16 is a cross-sectional view of the embodiment shown in FIG. 13 prior to insertion into a body passage.

Referring now to FIG. 16, illustrating the catheter bundle for the embodiment illustrated in FIGS. 13 and 14 prior to release from the catheter 68, the catheter 68 encircles the prosthesis 40'. In the interior of the prosthesis 40' is the guide wire catheter 86, with one or more of wires 103 which may be used to control the position of the folded portion of the annular rings 30. Outside of the guide wire catheter 86 are a pair of wires corresponding to the blocking wires 96 and 100.

Figure 17:
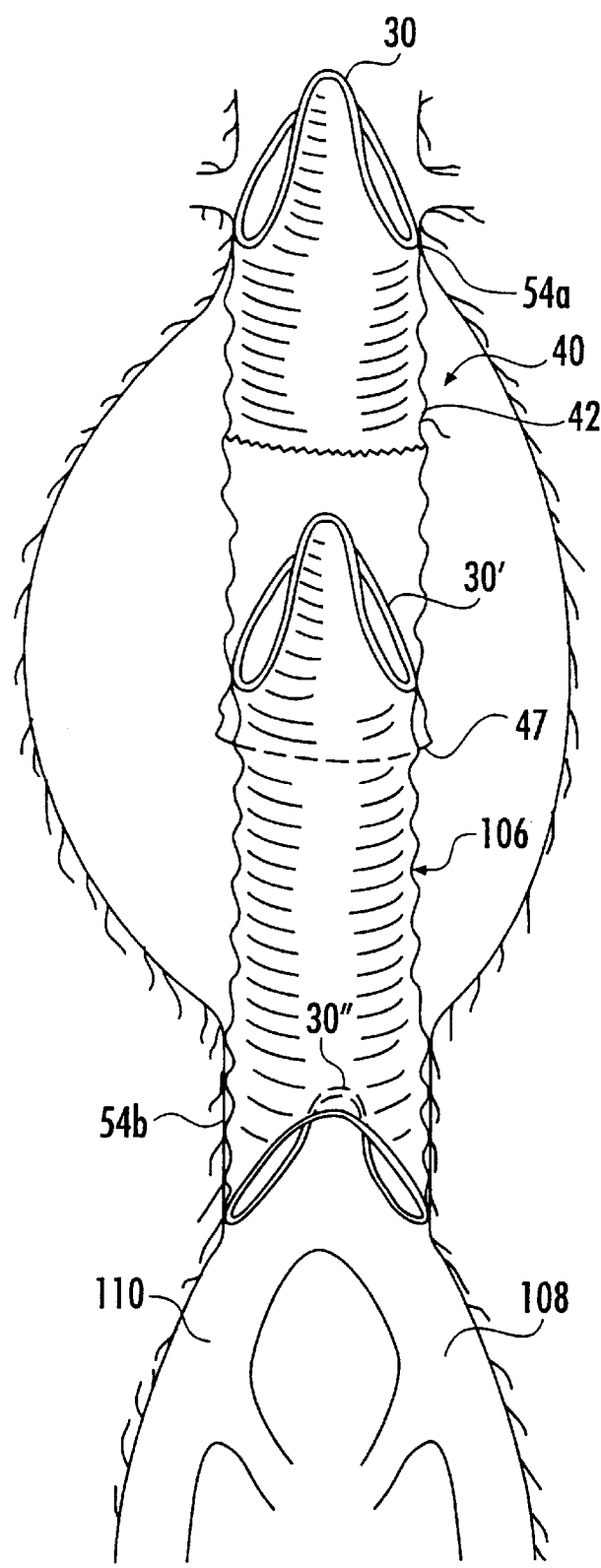
FIG. 17 is a front elevational view of another embodiment in place within a sectioned aortic bifurcation.

In accordance with another embodiment of the invention, the prosthesis 40 may be supplemented by one or more additional modules such as the prosthesis 106, shown in FIG. 17. The second prosthesis 106 telescopically engages the first prosthesis 40 using an annular ring 30 which expands outwardly against the resistance provided by the graft 42. The second prosthesis 106 includes an upper annular ring 30' and a lower annular ring 30". It is the upper annular ring 30' which engages the graft 42 while the lower annular ring 30" engages in the distal neck 54*b*. Because the amount of telescopic extension of the second prosthesis 106 into the first prosthesis 40 may be adjusted, a wide arrangement of different vessel longitudinal sizes can be accommodated.

Figure 23:
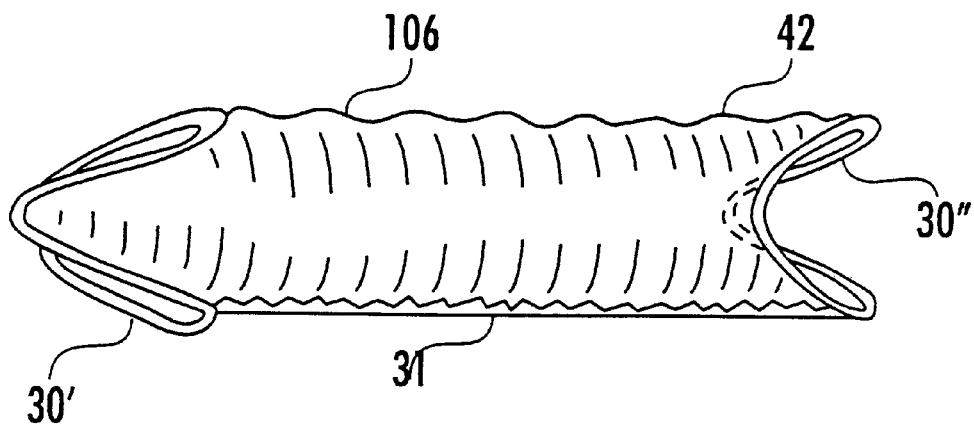
FIG. 23 is a partially sectioned front elevational view of another embodiment.

The prosthesis 106 including a pair of rings 30' and 30" may have a longitudinal torsion preventing wire 31 as shown in FIG. 23. The wire 31 may be wrapped around the rings 30' and 30" to control torsion or twisting of the prosthesis 106 about its longitudinal axis and to provide additional longitudinal support. The wire 31 is covered by the graft 42, either by positioning the wire 31 in the interior of the prosthesis 106 or by weaving the wire 31 through a graft 42 made of fabric. If desired, one or more additional wires 31 may be provided around the circumference of the rings 30' and 30".

The second prosthesis 106 may be located inside the first prosthesis using the guide wire 104 which stays in position after all of the wires utilized to position the first prosthesis have been removed. Thereafter the second prosthesis 106 may be run back to the same location using the guide wire 104 which stayed in place after the first prosthesis 40 was positioned.

The guide wire 104 maintains the opening of the graft as well. However, in practice the blood flow through the prosthesis 40 causes it to act like an open, expanded, windsock. Therefore, using the guiding action of the guide wire 104, the second prosthesis 106 can engage the interior surface of the graft 42. Thus, the combination of the two prostheses 40 and 106 can adjustably span between the necks 54*a* and 54*b* by altering the extension of the prosthesis 106 into the prosthesis 40.

Figure 22:
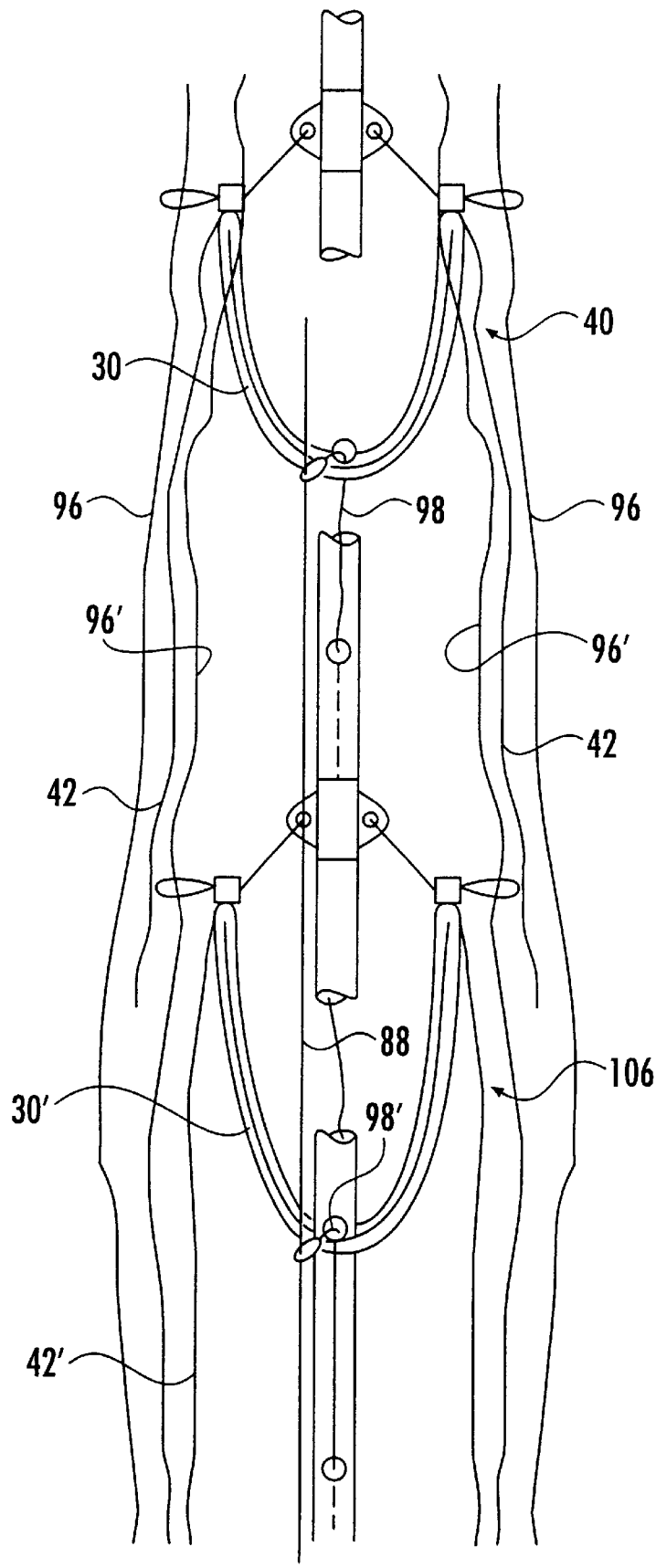
FIG. 22 is a front elevational view corresponding to FIG. 14 showing an alternate embodiment.

The prostheses 40 and 106 may also be positioned using the mechanism 84, as shown in FIG. 22. The prosthesis 106 may be inserted into the patient, already located within the prosthesis 40, using an additional set of blocking wires 96'. The blocking wires 96' extend through the lower loops 94 and through the interior of the prosthesis 40. In this way, the prosthesis 106 may be manipulated independently, adjustably telescoping within the prosthesis 40. In this case, the wires 98 and 98' may run separately to the exterior of the patient to facilitate independent manipulation of the prostheses 40 and 106.

Figure 18:
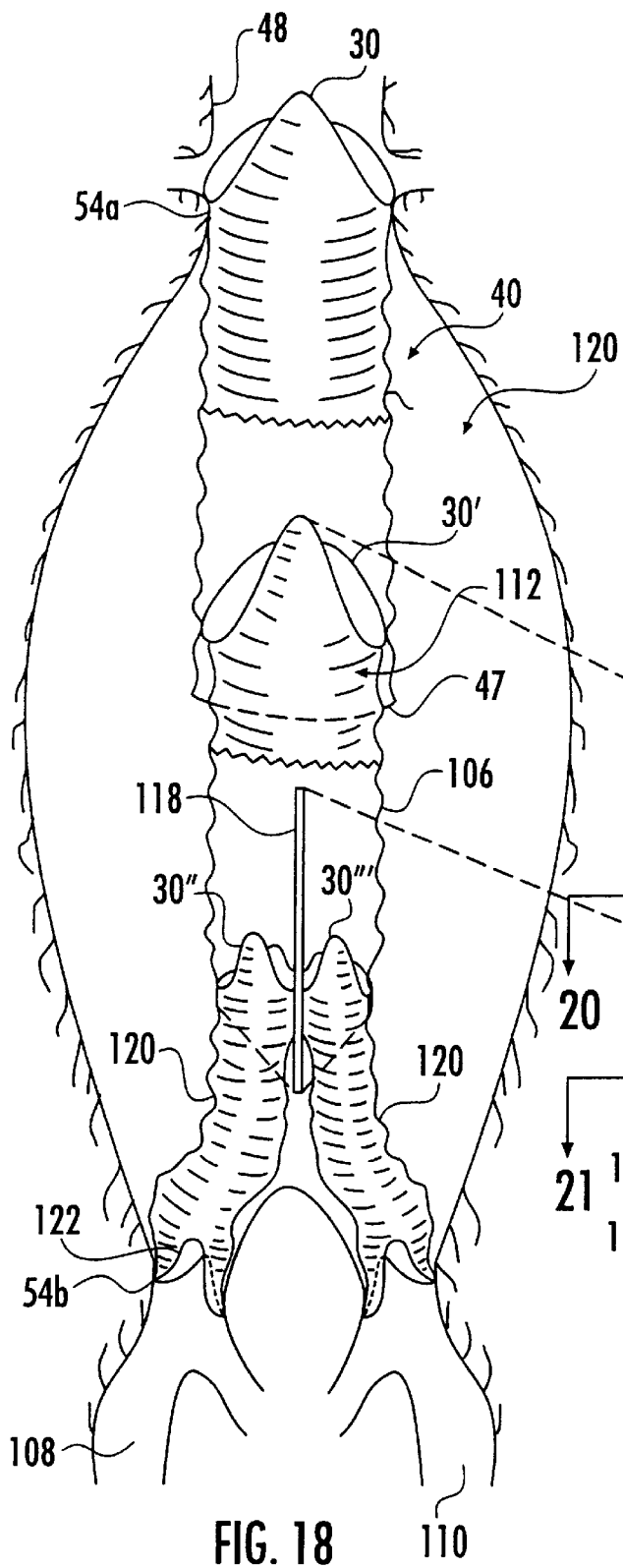
FIG. 18 is a front elevational view of still another embodiment in place within a sectioned aortic bifurcation.
Figure 19:
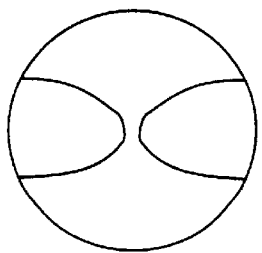
FIG. 19 is an enlarged front elevational view of a module shown in FIG. 18.

A prosthesis similar to those described above may also be used to provide a bifurcated stent 120, shown in FIG. 18, which extends from the abdominal aorta 48 and its associated neck 54*a* past the lower neck 54*b* and into the iliac or pelvic arteries 108 and 110. Again, a prosthesis 40 as described above is provided for engagement with the neck 54*a*. Instead of the prosthesis 106 described previously, a specially configured prosthesis 112 may be utilized next. The prosthesis 112, shown in FIG. 19, may include a ring 30 on its upper end and a pair of rings 114 on its lower end. The rings 114 need not be compressed since they simply maintain the lower end of the prosthesis 112 in an open configuration.

Figure 20:
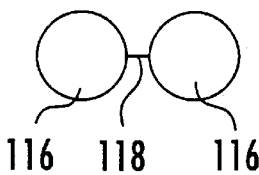
FIG. 20 is a cross-sectional view taken generally along the line 20—20 in FIG. 19.
Figure 21:
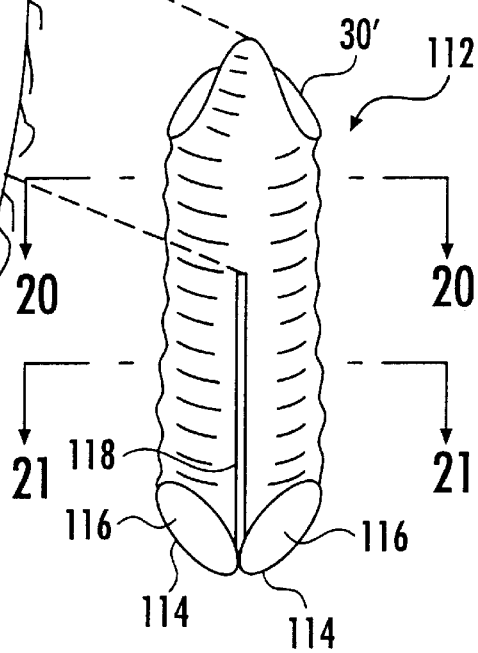
FIG. 21 is a cross-sectional view taken generally along the line 21—21 in FIG. 19.

As shown in FIGS. 20 and 21, the upper end of the prosthesis 112 may have a circular configuration of the type described previously. The lower end may have a double tubular configuration including a pair of passages 116 defined by a connection 118 which extends axially along the prosthesis 112 to form two separate chambers 116 terminated by the rings 114. The rings 114 may be oriented at an angle to the axis of the prosthesis 112 to allow easy entrance from the iliac arteries 108 and 110.

A pair of smaller diameter prostheses 120 are bilaterally inserted through each iliac artery 108 or 110 for engagement with the prosthesis 112. Particularly, the upper rings 30" enter through rings 114 and pass into the interior of the passages 116 where they expand outwardly against the graft 42. At the same time the other end 122 of each prosthesis 120 engages the neck 54b at the iliac artery 108 or 110. One of the prostheses 120 may be inserted using the same guide wire utilized to position the previously positioned prostheses. However, the other prosthesis 120 must be positioned independently of that guide wire. For this purpose, x-ray proof materials may be utilized on the rings 30" and 114 to facilitate location of the rings 114 and passage through them by the prosthesis 120 which is inserted without the previously located guide wire.

With the apparatus and techniques described above, it should be apparent that the prostheses 40, 40', 120 may be positioned without substantially blocking the flow of blood even during the surgical procedure. Moreover, the prostheses 40, 40' or 120 are configured so as not to substantially interfere with intersecting vessels such as the renal arteries. At the same time a modular approach may be utilized to adjust for different physiologies. This in combination with the fact that the annular ring 30 need never extend to its fully undeformed configuration, means that it is not necessary to stock a variety of different stents. Instead it is possible to have a relatively limited or even a single set of sizes which can be adapted to a variety of patient conditions.

Because of the fact that the rings 30 have a C-shaped configuration in position in the body passage, it is possible to locate the prosthesis in a relatively narrow neck 54 region. Since the ring 30 remains in its compressed configuration in use, it adapts for short term and long term distension of the treated passage. Moreover, because of the constantly applied spring bias pressure of the rings 30, good sealing contact is maintained between the rings 30 (and the prostheses) and the wall of body passage even if the passage is irregularly shaped.

With the positioning techniques described above it is possible to accurately position the prosthesis as desired within a body passage. This is because the prosthesis is maintained in a first compressed configuration as it is loaded and transported to the desired location so that it may be positioned without having to overcome friction between the prosthesis and the vessel passage. Once in its desired position, the prosthesis can be activated to engage the wall. It is also possible to reposition the prosthesis after the wall has been engaged if desired. This facilitates accurate positioning and avoids the need to attempt to reposition the prosthesis after it has irreversibly assumed the expanded configuration. In this way the surgeon has considerable control (through guide wire and tubes, for example) to accurately position a prosthesis at its most effective position.

Figure 24:
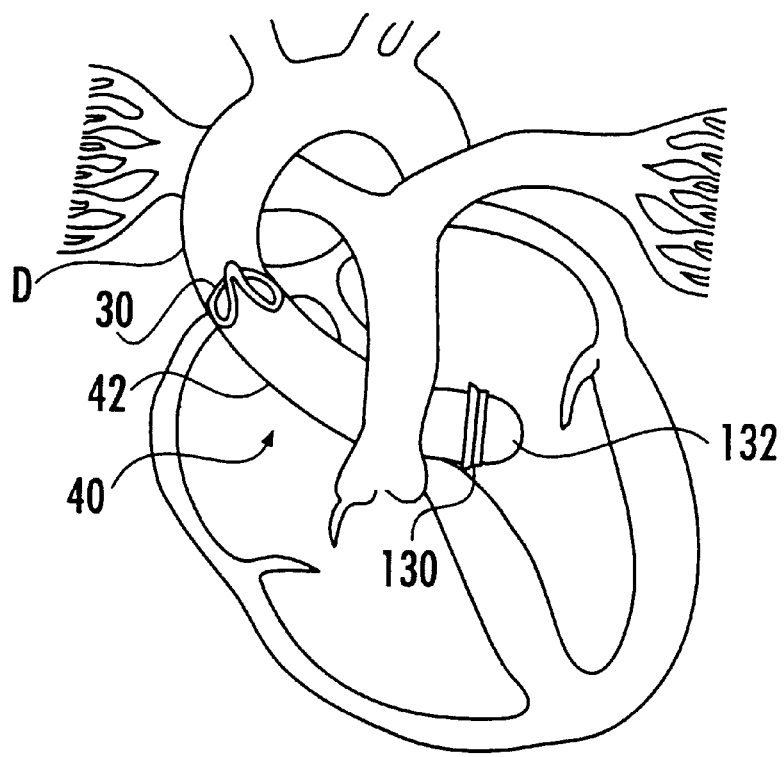
FIG. 24 is a front elevational view of a prosthetic device positioned within a sectioned heart.

The prosthesis 40 may also be utilized to replace a diseased portion of the ascending aorta as indicated in FIG. 24. An annular ring 30 may be positioned in the remaining portion of the ascending aorta "D" after a portion of the aorta has been surgically removed. The clamping ring 30 secures itself to the inside surface of the aorta "D" as described previously. The clamping ring is connected to a tubular, flexible sleeve or graft 42 and the graft 42 in turn connects to a sewing ring 130 which facilitates connection to a mechanical heart valve 132. The details of the valve and the graft will be known to those of skill in the art and are described in U.S. Pat. No. 5,123,919, issued to Sauter et al., which is hereby expressly incorporated by reference herein.

The graft 42 may be any of a variety of lengths depending on the amount of tissue involved. The graft 42 could extend further than is illustrated and may be considerably shorter. For example, where it is only necessary to replace the heart valve, the graft 42 may amount to little more than a short flexible sleeve connecting the mechanical valve 132 to the ring 30.

While the present invention has been described with respect to a limited number of preferred embodiments, those skilled in the art will appreciate numerous modifications and variations therefrom. For example, while the device has been described in some instances as a vascular stent for treating aneurysms, the invention may be applicable to securing any device to an internal passage. In addition, it should be appreciated that certain embodiments of the present invention may have only one or more of the advantages described above or may instead have other advantages not specifically mentioned herein. It is intended that the appended claims cover all such modifications and variations as fall within the true spirit and scope of the appended claims.

What is claimed:

1. A device for retaining a prosthesis within a body passage comprising an annular, resilient element, wherein said element is formed by overlapping a plurality of windings of wire radially on top of one another around a common core and connecting the windings together to form a bundle, said wire being sized to decrease the minimum bending diameter of said element.

2. The device of claim 1 wherein when in said undeformed state said resilient element has a circular cross-section.

3. The device of claim 1 wherein said wire is formed of a superelastic phase nickel-titanium alloy.

4. The device of claim 1 wherein said element is adapted to be situated inside a body passage in a C-shaped configuration, folded about a diametric axis of said element.

5. A device for retaining a prosthesis within a body passage comprising an annular, resilient element, said element formed from a plurality of winding of wire, said element being folded into a C-shape around a diametrical axis to form a pair of loops extending outwardly from said diametrical axis and arranged one over the other.

* * * * *

UNITED STATES PATENT AND TRADEMARK OFFICE
CERTIFICATE OF CORRECTION

PATENT NO.    : 6,740,111 B1
DATED         : May 25, 2004
INVENTOR(S)   : Karl-Lutz Lauterjung It is certified that error appears in the above-identified patent and that said Letters Patent is hereby corrected as shown below:

Column 10,
Line 49, "winding" should be -- windings --.

Signed and Sealed this

Twenty-seventh Day of July, 2004

JON W. DUDAS
*Acting Director of the United States Patent and Trademark Office*